United States Patent [19]
Park et al.

[11] Patent Number: 6,024,954
[45] Date of Patent: *Feb. 15, 2000

[54] COMPOSITIONS AND METHODS FOR DISINFECTING CONTACT LENSES AND PRESERVING CONTACT LENS CARE PRODUCTS

[75] Inventors: John Y. Park, Santa Ana; Lin Peng, Tustin; Daniel P. Cafaro, Santa Ana; Anthony J. Dziabo, Lake Forest, all of Calif.

[73] Assignee: Allergan, Waco, Tex.

[*] Notice: This patent is subject to a terminal disclaimer.

[21] Appl. No.: 08/692,867

[22] Filed: Aug. 2, 1996

Related U.S. Application Data

[63] Continuation-in-part of application No. 08/353,782, Dec. 12, 1994, Pat. No. 5,648,074.

[51] Int. Cl.$^7$ ................................................. A61K 38/54
[52] U.S. Cl. ................... 424/94.2; 424/94.1; 424/94.63; 424/661; 435/264; 514/56; 514/54; 514/57
[58] Field of Search ................................. 424/94.1, 94.2, 424/94.63, 661; 435/264; 514/56, 54, 57

[56] References Cited

U.S. PATENT DOCUMENTS

| | | | |
|---|---|---|---|
| Re. 23,218 | 4/1950 | Levy | 162/87 |
| Re. 31,779 | 12/1984 | Alliger | 252/187.23 |
| Re. 32,672 | 5/1988 | Huth et al. | 435/264 |
| 2,436,134 | 2/1948 | Aston | 423/477 |
| 2,477,631 | 8/1949 | Levy et al. | 162/87 |

(List continued on next page.)

FOREIGN PATENT DOCUMENTS

| | | |
|---|---|---|
| 520668 | 12/1987 | Austria . |
| 1156420 | 11/1983 | Canada . |
| 0082798 | 6/1983 | European Pat. Off. . |
| 0147100 | 7/1985 | European Pat. Off. . |
| 0168253 | 1/1986 | European Pat. Off. . |
| 0196075 | 1/1986 | European Pat. Off. . |
| 0199385 | 10/1986 | European Pat. Off. . |
| 0209071 | 1/1987 | European Pat. Off. . |
| 0240315 | 10/1987 | European Pat. Off. . |
| 0279401 | 2/1988 | European Pat. Off. . |
| 0255041A1 | 5/1988 | European Pat. Off. . |
| 0278224 | 8/1988 | European Pat. Off. . |
| 0384666 | 8/1990 | European Pat. Off. . |
| 0426489 | 5/1991 | European Pat. Off. . |
| 36260821A1 | 11/1988 | Germany . |
| 2097913 | 10/1990 | Japan . |
| 1269677 | 4/1982 | United Kingdom . |
| 2094992 | 9/1982 | United Kingdom . |
| 2139260 | 11/1984 | United Kingdom . |
| 2173017 | 10/1986 | United Kingdom . |
| 2187748 | 9/1987 | United Kingdom . |
| 2151039 | 7/1988 | United Kingdom . |
| 8404681 | 12/1984 | WIPO . |
| WO 804107 | 9/1985 | WIPO . |
| WO 8605695 | 10/1986 | WIPO . |
| WO 8911878 | 12/1989 | WIPO . |
| WO9006126 | 6/1990 | WIPO . |
| 9304706 | 3/1993 | WIPO . |
| WO94/13332 | 12/1993 | WIPO . |
| 9602264 | 2/1996 | WIPO . |

OTHER PUBLICATIONS

Chemical Abstracts Selects: Issue 2, 1987.
Eudragit L Data Sheet (Info L–2/e).
Siu et al, "Effect of Succinylation on the Protein Quality and Urinary Excretion of Bound and Free Amino Acids", J. AgricFood Chem 1982, 30; 1179–1183.
Communications to the Editor, "Stabilization of Microbial Proteases against Autolysis Using Acylation with Dicarboxylic Acid Anhydrides" Biotechnology and Bioengineering, vol. XXIV, pp. 483–486 (1982).
Kennedy et al, "The Oxidation of Organic Substances by Potassium Peroxymonosufate",J. Organic Chemistry 25:1901–1906 (1960).
Polymers Letters Edition, "A Study of Ozone Attack On Elastomer Surfaces By Attenuated Total Reflectance Spectroscopy", vol. 12, pp. 28–286 (1974).
Manivannan et al, Peroxo Salts As Initiators Of Vinyl Polymerization–II Eur. Polym. J. vol. 23, No. 4, pp. 311–313 (1987).
Evans et al, Phase Transfer Controlled Selective Oxidation of Diarylsulfides to Diarylsulfoxidos Using Potassium Hydrogen Persulfase, Synthetic Communications, 16(10), 1207–1216 (1986).
Bloch et al, Epoxidation of Alkenes with Potassium Hydrogen Persulfate J. Org. Chem. 1985, 50:1544–1545.
Ball, Jr. et al., "Acylation of Egg White Proteins with Acetiv Anhydride and Succinic Anydride", Poultry Science 1982 61:1041–1046.
W. Masschelein, "Preparation of Pure Chlorine Dioxide", vol. 6, No. Jun. 2, 1967.
I. Klotz, "Succinylation", Methods in Enzymology, vol. XI, Enzyme Structure, 1967, 576–580.
De Poorter et al, "Oxone As Oxygen Donor In The Catalytic Hydroxylation of Saturated Hydrocarbons", Tetrahedron Letters, vol. 26 No. 3 pp. 4459–4462 (1985).
Trost et al, "Chemoselective Oxidation of Sulfides to Sulfones With Potassium Hydrogen Persulfate", Tetrahedron Letters vol 22 No., 14, pp. 1287–1290 (1981).

*Primary Examiner*—Jean C. Witz
*Attorney, Agent, or Firm*—Frank J. Uxa

[57] ABSTRACT

Compositions for disinfecting contact lenses include a liquid medium containing a chlorite component, preferably a water soluble chlorite component, in a contact lens disinfecting amount, and a polyanionic component, preferably a water soluble polyanionic component, in an amount effective to do at least one of the following: inhibit formation of protein deposit material on a contact lens immersed in the composition; reduce the toxicity of the composition to the human eye, and reduce the damage to a contact lens caused by immersing the contact lens in the composition. The composition has a viscosity of less than 50 cps at 25° C., an osmolality of at least about 200 mOsmol/kg, and preferably a pH in the range of about 6 to about 9.

32 Claims, No Drawings

U.S. PATENT DOCUMENTS

| | | | |
|---|---|---|---|
| 3,123,521 | 3/1964 | Wentworth | 424/615 |
| 3,278,447 | 10/1966 | McNicholas | 252/186.21 |
| 3,386,915 | 6/1968 | Rutschi | 210/754 |
| 3,450,814 | 6/1969 | Bechtold et al. | 514/54 |
| 3,563,702 | 2/1971 | Partridge | 423/478 |
| 3,585,147 | 6/1971 | Gordon | 252/187.21 |
| 3,591,515 | 7/1971 | Lovely | 252/186.22 |
| 3,622,479 | 11/1971 | Schneider | 210/748 |
| 3,763,006 | 10/1973 | Callerame | 205/556 |
| 3,819,828 | 6/1974 | McCoy | 424/70.4 |
| 3,910,296 | 10/1975 | Karageozian et al. | 134/2 |
| 3,912,451 | 10/1975 | Gaglia et al. | 422/30 |
| 3,920,810 | 11/1975 | Rankin | 424/78.04 |
| 4,011,941 | 3/1977 | Parsons | 206/5.1 |
| 4,029,817 | 6/1977 | Blanco et al. | 514/496 |
| 4,084,747 | 4/1978 | Alliger | 422/327 |
| 4,104,190 | 8/1978 | Hartshorn | 252/187.21 |
| 4,123,376 | 10/1978 | Gray | 510/307 |
| 4,146,496 | 3/1979 | Gray | 8/111 |
| 4,171,526 | 10/1979 | Wong et al. | 346/23 |
| 4,202,740 | 5/1980 | Stoner et al. | 205/701 |
| 4,236,992 | 12/1980 | Themy | 204/229.7 |
| 4,361,471 | 11/1982 | Kosarek | 210/748 |
| 4,386,160 | 5/1983 | Branner-Jorgensen | 435/221 |
| 4,436,730 | 3/1984 | Ellis et al. | 514/57 |
| 4,456,510 | 6/1984 | Murakami | 205/556 |
| 4,459,217 | 7/1984 | Bogie | 510/117 |
| 4,496,452 | 1/1985 | Bianchi | 204/266 |
| 4,499,077 | 2/1985 | Stockel et al. | 424/661 |
| 4,557,925 | 12/1985 | Lindahl et al. | 424/482 |
| 4,560,491 | 12/1985 | Sherman | 514/275 |
| 4,568,517 | 2/1986 | Kaspar et al. | 422/30 |
| 4,585,482 | 4/1986 | Tice et al. | 106/15.05 |
| 4,614,549 | 9/1986 | Ogunbuyi et al. | 134/19 |
| 4,618,444 | 10/1986 | Hudson et al. | 8/111 |
| 4,654,208 | 3/1987 | Stockel et al. | 424/78.08 |
| 4,689,169 | 8/1987 | Mason et al. | 252/186.24 |
| 4,689,215 | 8/1987 | Ratcliff | 424/53 |
| 4,690,773 | 9/1987 | Ogunbuyi et al. | 435/264 |
| 4,731,192 | 3/1988 | Kenjo et al. | 510/113 |
| 4,767,559 | 8/1988 | Kruse et al. | 510/114 |
| 4,786,492 | 11/1988 | Ratcliff | 424/53 |
| 4,788,053 | 11/1988 | Ratcliff | 424/53 |
| 4,792,442 | 12/1988 | Ratcliff | 424/53 |
| 4,837,009 | 6/1989 | Ratcliff | 424/53 |
| 4,855,135 | 8/1989 | Ratcliff | 424/661 |
| 4,861,514 | 8/1989 | Hutchings | 510/102 |
| 4,986,990 | 1/1991 | Davidson et al. | 424/665 |
| 4,997,626 | 3/1991 | Dziabo et al. | 422/37 |
| 5,076,960 | 12/1991 | Hutchings et al. | 252/186.33 |
| 5,077,258 | 12/1991 | Phillips | 502/321 |
| 5,078,908 | 1/1992 | Ripley et al. | 252/187.21 |
| 5,122,598 | 6/1992 | della Valle et al. | 536/20 |
| 5,129,999 | 7/1992 | Holland et al. | 205/701 |
| 5,135,623 | 8/1992 | Dziabo et al. | 205/701 |
| 5,145,644 | 9/1992 | Park et al. | 422/28 |
| 5,147,861 | 9/1992 | della Valle et al. | 514/54 |
| 5,152,912 | 10/1992 | Dziabo et al. | 510/112 |
| 5,185,161 | 2/1993 | Davidson et al. | 424/665 |
| 5,197,636 | 3/1993 | Mitchell et al. | 222/190 |
| 5,212,192 | 5/1993 | Missel et al. | 514/54 |
| 5,229,128 | 7/1993 | Haddad et al. | 424/427 |
| 5,264,460 | 11/1993 | Jakobson et al. | 514/786 |
| 5,279,673 | 1/1994 | Dziabo et al. | 134/26 |
| 5,300,296 | 4/1994 | Holly et al. | 424/427 |
| 5,302,399 | 4/1994 | Otagiri et al. | 424/493 |
| 5,306,440 | 4/1994 | Ripley et al. | 252/186.33 |
| 5,330,752 | 7/1994 | Park et al. | 424/94.4 |
| 5,336,434 | 8/1994 | Park et al. | 252/187.21 |
| 5,336,643 | 8/1994 | Park et al. | 252/187.21 |
| 5,338,480 | 8/1994 | Dziabo et al. | 252/187.21 |
| 5,382,599 | 1/1995 | Rupp et al. | 514/547 |
| 5,424,078 | 6/1995 | Dziabo et al. | 424/661 |
| 5,648,074 | 7/1997 | Park et al. | 424/94.2 |

COMPOSITIONS AND METHODS FOR DISINFECTING CONTACT LENSES AND PRESERVING CONTACT LENS CARE PRODUCTS

RELATED APPLICATION

This application is a continuation-in-part of application Ser. No. 08/353,782, filed Dec. 12, 1994, now U.S. Pat. No. 5,648,074, which application is incorporated in its entirety herein by reference.

BACKGROUND OF THE INVENTION

This invention relates to compositions and methods useful in disinfecting contact lenses and in preserving contact lens care products. More particularly, the invention relates to compositions and methods in which contact lenses are disinfected and/or contact lens care products are preserved using compositions containing chlorite components and polyanionic components.

The use of chlorine dioxide dissolved in an aqueous liquid medium to disinfect contact lenses has previously been suggested.

Park et al U.S. Pat. No. 5,336,434 and Dziabo et al U.S. Pat. No. 5,338,480 disclose contact lens disinfecting using chlorine dioxide in which delayed release components are used to delay the release of chlorine dioxide activators, chlorine dioxide destroying components and/or cleaning enzyme components. Various delayed release components are disclosed, for example, soluble cellulose ethers such as methylcellulose, methylhydroxypropylcellulose, methylhydroxyethylcellulose, hydroxypropylcellulose, hydroxyethylcellulose and sodium carboxymethylcelluloses; cellulose esters such as cellulose acetate phthalate and hydroxypropylmethyl-cellulose phthalate; polymers derived from at least one of acrylic acid, acrylic acid esters, methacrylic acid and methacrylic acid esters such as methacrylic acid-methyl methacrylate copolymer (for example, that sold by Rohm Pharma under the trademark Eudragit L 100) and methacrylic acid-ethyl acrylate copolymers (for example, that sold by Rohm Pharma under the trademark Eudragit L 30D); polymers derived from methyl vinyl ether and maleic acid anhydride; polyvinylpyrrolidone; polyvinyl alcohols and the like and mixtures thereof. However, neither of these patents discloses that such delayed release components are effective to delay or prevent proteinaceous deposit formation on the contact lens being disinfected or to reduce the toxicity of the disinfecting composition to the human eye.

Dziabo et al U.S. Pat. No. 5,424,078 discloses the use of stabilized chlorine dioxide as a preservative for ophthalmic formulations. Although these preserved formulations provide many benefits, some questions remain about the long term use of stabilized chlorine dioxide in the eye in conjunction with contact lenses. New compositions providing additional and/or enhanced benefits are desirable.

Although polyanionic polymers, such as carboxymethyl cellulose, have been used for rewetting eye drop formulations, for example, to relieve or protect against dry eye irritation, such formulations have been used in single dose product configurations. A multi-dose rewetting eye drop product is highly advantageous, providing convenience, simplicity and low cost to users. However, such a multi-dose formulation has not been provided due to the lack of an adequate, non-cytotoxic and non-irritating preservative for such formulations.

It would be advantageous to provide a new contact lens disinfection system and/or a new contact lens storage system and/or a new preservative system for contact lens care products.

SUMMARY OF THE INVENTION

New compositions, and methods for use thereof, which include a combination of chlorite components and polyanionic components have been discovered. Thus, in accordance with the present invention, the antimicrobial properties of chlorite components are utilized while, at the same time, the potentially disadvantageous effects of chlorite components in the eye and/or on the contact lens being treated is inhibited and/or enhanced lubricity is provided. The present compositions are straightforward, easy and inexpensive to produce and use and provide outstanding benefits. Because the presently useful components are preferably water soluble, the present compositions can be utilized in very easy to practice methods for disinfecting contact lenses and preserving contact lens care products. A single bottle or one step contact lens disinfection system is envisioned. Thus, user compliance is very easily obtained. In addition, a multi-dose eye drop formulation and a contact lens, in particular daily disposable contact lens, storage medium are envisioned. In short, the present compositions and methods provide for highly effective and advantageous contact lens disinfecting and contact lens care product preserving while reducing, or even substantially eliminating, the potentially disadvantageous effects of the chlorite component on the eye and/or on the lens being treated.

In one broad aspect of the present invention, compositions comprising a liquid medium, a chlorite component and a polyanionic component are provided. The chlorite component is present in the liquid medium in a contact lens disinfecting amount. The polyanionic component is included in the liquid medium in an amount, preferably of at least 0.01% by weight per volume (w/v) of the composition, effective to do at least one of: inhibit formation of protein deposit material on a contact lens immersed in the composition, provide cleaning of a contact lens immersed in the composition, reduce the toxicity of the composition to the human eye, and reduce the damage to a contact lens caused by immersing the contact lens in the composition. The composition preferably has a viscosity of less than 50 cps at 25° C. and an osmolality of at least about 200 mOsmol/kg. More preferably, the composition has a pH in the range of about 6 to about 8 or about 9 so that the composition is ophthalmically acceptable.

A material is "ophthalmically acceptable" if the material can be placed in or on a mammalian, preferably, human, eye with or without a contact lens without causing any significant discomfort, irritation or harm to the eye.

The polyanionic component and any precursor thereof preferably do not act as a delayed release component, that is do not act to substantially (for a controlled or substantially predetermined period of time) delay the release of another component in the composition and any liquid-containing precursor thereof. In other words, the present polyanionic components are effective to provide one or more benefits and preferably are not employed, in the present invention, as delayed release components.

The liquid medium preferably comprises water, and the chlorite component and the polyanionic component are preferably water soluble. The polyanionic component is preferably present in an amount effective to reduce the toxicity of the composition to the human eye and/or reduce the damage to a contact lens caused by immersing the contact lens in the composition relative to the human eye toxicity and/or contact lens damage of a substantially identical composition without the polyanionic component.

In another broad aspect of the present invention, compositions comprising a liquid medium, and effective preserving amount of chlorite component and a polyanionic component are provided. The polyanionic component is present in an amount, preferably of at least 0.01% w/v, effective to enhance the lubricity of the composition, to reduce the mechanical irritation, e.g., awareness of contact lens wear, and to reduce the toxicity, for example, the cytotoxicity, of the composition to the human eye. The polyanionic component and any precursor thereof preferably do not act as a delayed release component, as discussed above. Thus, the present polyanionic components are effective to enhance lubricity and reduce toxicity and preferably are not employed, in the present invention, as delayed release components.

The liquid medium preferably comprises water, and the chlorite and the polyanionic component are preferably water soluble. The polyanionic component is preferably effective to enhance lubricity and reduce toxicity relative to the lubricity and toxicity of a substantially identical composition without the polyanionic component.

As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from the group consisting of polymeric materials having multiple anionic charges and mixtures thereof. Particularly useful anionic components are selected from anionic cellulose derivatives, anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers of amino acids (meaning to include polymers of amino acids, amino acid salts, and the like and mixtures thereof), and the like and mixtures thereof. Very useful polyanionic components are those selected from anionic cellulose derivatives and mixtures thereof, especially carboxymethylcelluloses.

The polyanionic component is preferably sufficiently anionic to interact with lysozyme, which is cationically charged, and is present with the contact lens immersed in the composition. This interaction is preferably sufficient to render the lysozyme soluble in the chlorite component-containing composition.

Methods for disinfecting contact lenses are included within the scope of the present invention. In one embodiment, the present methods comprise contacting a contact lens with a composition comprising a liquid medium containing a disinfecting amount of chlorite component and a polyanionic component as described herein.

Methods for storing contact lenses are included within the scope of the present invention. These methods comprise immersing a contact lens in a liquid medium containing a chlorite component in an effective preserving amount and a polyanionic component as described herein.

Methods involving in-the-eye use of chlorite component containing compositions are within the scope of the present invention. Such methods comprise providing a composition including a liquid medium, an effective preserving amount of chlorite component and a polyanionic component, as described herein, in an eye wearing a contact lens, for example, in the form of eye drops. Such providing preferably is effective to provide additional wetness, lubrication, reduction of mechanical irritation and/or cleaning in the eye, making it more easy and/or comfortable to wear the contact lens. The composition in this circumstance may be considered a rewetting or lubricant composition, and is preferably present in a multi-dose product configuration.

In addition, one or more other components can be added to the presently useful compositions to provide one or more further benefits and/or improvements to the contact lens being treated and/or to the wearer of the treated lens.

These and other aspects of the present invention will become apparent hereinafter, particularly when considered in conjunction with the following detailed description, examples and claims.

DETAILED DESCRIPTION OF THE INVENTION

The present compositions are applicable for treating all types of contact lenses. These contact lenses, for example, conventional hard contact lenses and soft contact lenses, may be made of any material or combination of materials and may have any suitable configuration.

One important feature of the present invention is the use of chlorite components as disinfectants and preservatives. Such chlorite components have, in the past, been suggested as precursors for disinfecting amounts of chlorine dioxide. In contrast, the chlorite components have been found to be useful in the present compositions as antimicrobial components without the production of chlorine dioxide. The present compositions preferably include substantially no free chlorine dioxide. As used herein, a disinfecting amount of chlorite component is such amount as will reduce the microbial burden or load by one log order in 3 hours or less, and preferably in 1 hour or less. Of course, the amount of chlorite component employed should not cause any substantial damage to the lens, and is preferably present in the compositions of the present invention in an amount of 0.15% or less.

Specific examples of chlorite components include stabilized chlorine dioxide (SCD), metal chlorites, such as alkali metal and alkaline earth metal chlorites, and the like and mixtures thereof. Technical grade sodium chlorite is a very useful chlorite component. The exact chemical composition of many chlorite components, for example, SCD, is not completely understood. The manufacture or production of certain chlorite components is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purogene® by Bio-Cide International, Inc.

The chlorite component may be included in a liquid medium at a predetermined concentration, e.g., to provide a disinfecting amount or a preserving amount of chlorite component in the liquid medium.

Any suitable polyanionic component may be employed in accordance with the present invention provided that it functions as described herein and has no substantial detrimental effect on the contact lens being disinfected or on the wearer of the disinfected contact lens. The polyanionic component is preferably ophthalmically acceptable at the concentrations used. The polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the presently useful liquid aqueous media, such as a liquid aqueous medium containing the polyanionic component and chlorite component.

The polyanionic component is preferably sufficiently anionic to interact with tear proteins, such as lysozyme, which are cationically charged. Such interaction is desirable to solubilize such tear proteins and/or to maintain such tear proteins soluble in the liquid medium. Such soluble tear proteins are believed to be less likely to form proteinaceous deposit materials on a contact lens.

A particularly useful class of polyanionic components are one or more polymeric materials having multiple anionic charges. Examples include:

metal carboxymethylcelluloses
metal carboxymethylhydroxyethylcelluloses
metal carboxymethylstarchs
metal carboxymethylhydroxyethylstarchs
hydrolyzed polyacrylamides and polyacrylonitriles
heparin
homopolymers and copolymers of one or more of:
   acrylic and methacrylic acids
   metal acrylates and methacrylates
   alginic acid
   metal alginates
   vinylsulfonic acid
   metal vinylsulfonate
   amino acids, such as aspartic acid, glutamic acid and the like
   metal salts of amino acids
   p-styrenesulfonic acid
   metal p-styrenesulfonate
   2-methacryloyloxyethylsulfonic acids
   metal 2-methacryloyloxethylsulfonates
   3-methacryloyloxy-2-hydroxypropylsulonic acids
   metal 3-methacryloyloxy-2-hydroxypropylsulfonates
   2-acrylamido-2-methylpropanesulfonic acids
   metal 2-acrylamido-2-methylpropanesulfonates
   allylsulfonic acid
   metal allylsulfonate and the like.

The present polyanionic components often can exist in the un-ionized state, for example, in the solid state, in combination with a companion or counter ion, in particular a plurality of discrete cations equal in number to the number of discrete anionic charges so that the un-ionized polyanionic component is electrically neutral. For example, the present un-ionized polyanionic components may be present in the acid form and/or in combination with one or more metals. Since the polyanionic components are preferably ophthalmically acceptable, it is preferred that the metal associated with the un-ionized polyanionic component be ophthalmically acceptable in the concentrations used. Particularly useful metals include the alkali metals, for example, sodium and potassium, the alkaline earth metals, for example, calcium and magnesium, and mixtures thereof. Sodium is very useful to provide the counter ion in the un-ionized polyanionic component. Polyanionic components which, in the un-ionized states, are combined with cations other than H$^+$ and metal cations can be employed in the present invention.

Particularly useful polyanionic components are selected from anionic cellulose derivatives, anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers derived from amino acids (meaning to include amino acids, amino acid salts, and the like and mixtures thereof) and mixtures thereof. Very useful polyanionic components are those selected from anionic cellulose derivatives and mixtures thereof, especially carboxymethylcelluloses.

The amount of polyanionic component employed is that amount effective to function as described herein. Preferably the polyanionic component is present in the composition of the invention in an amount of at least 0.01% w/v. The specific amount of such component used is not critical to the present invention provided that it functions as described herein. In addition, the amount of polyanionic component employed depends on a number of factors, for example, the specific polyanionic component being employed, the chlorite component concentration being employed and the application of or end result desired from the composition. In addition, excessive amounts of polyanionic component are preferably to be avoided since this may be wasteful and unnecessary and may have an adverse impact on the wearer of the disinfected contact lens. Preferably, the polyanionic component is present in an amount of at least about 0.01% w/v or at least about 0.05% w/v to about 5% w/v or about 2% w/v or about 1% w/v.

Many of the materials useful as polyanionic components in the present invention have previously been used as delayed release components. Therefore, it is important to note that the ability of a material to act to reduce toxicity or harm to the lens or enhance lubricity is substantially different from and independent of the ability of a material to act as a delayed release component. Preferably, in the present compositions and methods, the polyanionic components and precursors thereof (for example, the polyanionic components in un-ionized (e.g. solid) forms do not act as delayed release components for any other components in the chlorite component containing compositions.

The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution. During the composition-contact lens contacting step or steps, for example, during the contact lens disinfecting contacting, the aqueous liquid medium preferably has a pH in the range of about 6 to about 9 or about 10, more preferably about 6 to about 8, and still more preferably about 7.5. The liquid medium preferably has a ophthalmically acceptable tonicity level, for example, of at least about 200 mOsmol/kg, more preferably in the range of about 200 to about 400 mOsmol/kg.

The liquid media containing the chlorite components and polyanionic components preferably have viscosities of less than 50 centipoise (cps) at 25° C., and more preferably less than about 25 cps or about 20 cps at 25° C.

In order to insure that the pH of the aqueous liquid medium is maintained within the desired range, the aqueous liquid medium may include at least one buffer component. Although any suitable buffer component may be employed, it is preferred to select such component so as not to produce a significant amount of chlorine dioxide. It is preferred that the buffer component be inorganic. Alkali metal and alkaline earth metal buffer components are advantageously used in the present invention.

Further, in order to avoid possible eye irritation, it is preferred that the presently useful liquid media have an osmolality (a measure of tonicity) of at least about 200 mOsmol/kg, preferably in the range of about 200 to about 350 or about 400 mOsmol/kg. In an especially useful embodiment, the osmolality or tonicity of the liquid medium substantially corresponds to the tonicity of the fluids of the eye, in particular the human eye.

Any suitable ophthalmically acceptable tonicity component or components may be employed, provided that such component or components are compatible with the other ingredients of the liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The amount of ophthalmically acceptable tonicity component utilized can vary widely. In one embodiment, the tonicity component is preferably present in the liquid medium in an amount in the range of about 0.5 to about 0.9 weight/volume percent of the formulation.

Typical of ophthalmically acceptable inorganic salt tonicity components are alkali metal chlorides and alkaline earth metal chlorides, such as sodium chloride, potassium chloride, calcium chloride and magnesium chloride.

In one particularly useful embodiment, the present compositions include mineral components, such as sodium components, potassium components, magnesium components and calcium components, which are typically present in human tears. Such mineral components provide the present compositions with enhanced contact lens wearability properties relative to similar or substantially identical compositions without such mineral components. For example, the present compositions including these mineral components have been found to enhance the ability of eyes to wear contact lenses treated with such compositions, relieve and/or sooth tired eyes wearing such lenses, and/or in general, advantageously facilitate the wearing of such lenses.

The mineral components, and in particular, potassium, magnesium, calcium components, are preferably water soluble and are preferably present in amounts of at least about 50%, more preferably of about 50% to 200%, of the concentration of the components (based on the metal ion) in the average human tear fluid. Such average human tear fluid typically includes a potassium ion ($K^+$) concentration of 18.21 millimolar; a magnesium ion ($Mg^{++}$) concentration of 0.30 millimolar; and a calcium ion ($Ca^{++}$) concentration of 0.70 millimolar.

In another useful embodiment, the present compositions include an effective amount of a colorant component to provide the composition with a distinctive color. Although any suitable colorant may be employed, vitamin B-12 is particularly useful, for example, because of the distinctive rose color it imparts to the present compositions. The amount of vitamin B-12 in the present compositions preferably is in the range of about 0.0005% (w/v) to about 0.005% (w/v), more preferably about 0.0008% (w/v) to about 0.001% (w/v).

One or more additional components can be included in the presently useful liquid media. Such additional component or components are chosen to impart or provide at least one beneficial or desired property to the liquid media. Such additional components may be selected from components which are conventionally used in one or more contact lens care compositions and which do not detrimentally interact with the chlorite component or the polyanionic component or any other component or components present in the compositions. Examples of such additional components include cleaning agents, wetting agents, nutrient agents, sequestering agents, viscosity builders, contact lens conditioning agents, antioxidants, and the like. These additional components may each be included in the liquid medium in an amount effective to impart or provide the beneficial or desired property to the liquid medium. For example, such additional components may be included in the presently useful liquid media in amounts similar to the amounts of such components used in other, e.g., conventional, contact lens care products.

Examples of useful sequestering agents include disodium ethylene diamine tetraacetate, alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

Examples of useful antioxidants include sodium metabisulfite, sodium thiosulfate, N-acetylcysteine, butylated hydroxyanisole, butylated hydroxytoluene and mixtures thereof.

In the event deposit material is formed on a contact lens in spite of the polyanionic component, the present compositions may include (1) a surfactant component in an amount effective to remove deposit material from a contact lens and/or (2) an enzyme component in an amount effective to remove deposit material from a contact lens.

The deposit material to be removed may be formed in-the-eye while the contact lens is being worn and/or during the disinfecting processing. Thus, although the polyanionic components are preferably effective to inhibit the formation of proteinaceous deposit material on a contact lens being treated some such deposit material may be formed during the contacting with chlorite component.

Among the types of deposit material that form on contact lenses, for example, during normal use in-the-eye, are proteinaceous deposit material, mucin-based deposit material, lipid-based deposit material and carbohydrate-based deposit material. One or more types of deposit material may be present on a single contact lens.

In one embodiment, the present compositions further include a surfactant component in an amount effective to at least facilitate the cleaning or removing of deposit material from contact lens immersed in, or contact with, the composition or the chlorine dioxide-containing composition derived therefrom. Preferably, the surfactant components used are stable in the present compositions.

In a particularly useful embodiment, the surfactant component has enhanced stability in the present compositions relative to an ethylene oxide, propylene oxide block copolymer having substantially the same contact lens cleaning efficacy as the surfactant component being employed. That is, the amount of surfactant component employed is more stable than an amount of an ethylene oxide, propylene oxide block copolymer having substantially the same contact lens cleaning efficacy as the amount of the surfactant component being employed. The surfactant component employed is preferably other than an ethylene oxide, propylene oxide block copolymer, since such block copolymers have been found to be somewhat unstable, for example, after storing the present compositions including such surfactants for relatively long periods of time.

Particularly useful surfactant components are selected from sulfates, sulfonates, alkyl polyglucosides and mixtures thereof. A number of such surfactant components are well known and are commercially available.

Specific examples of useful sulfate-containing surfactant components include alkyl sulfate salts of alkali metals and alkaline earth metals. The alkyl groups of such salts preferably have about 8 to about 20 or about 30 carbon atoms. It is preferred that the surfactant component be substantially free of ether groups, which may be particularly prone to interact with (and detrimentally effect) the chlorine dioxide precursor. A particularly useful sulfate-containing surfactant component is sodium dodecyl sulfate.

Specific examples of useful sulfonate-containing surfactant components include alkyl-containing sulfonates of alkali metals and alkaline earth metals. The alkyl groups of such salts can have about 8 to about 20 or about 30 or more carbon atoms. Such components may also include one or more aromatic hydrocarbon oxide groups, such as phenyloxide groups, without substantially detrimentally affecting the surfactant's stability. A particularly useful sulfonate-containing surfactant component is disodium alkyl diphenyloxide disulfonate.

The alkyl groups of the presently useful alkyl polyglucoside surfactant components preferably have about 8 to about 20 or about 30 carbon atoms. A particularly useful alkyl polyglucoside surfactant component is decyl polyglucoside.

In general, the surfactant component is effective to reduce the surface tension of the liquid medium in which it is contained (relative to the liquid medium without the surfactant component). The specific concentration of surfactant component in the present compositions depends on a number of factors, for example, the specific surfactant component being employed, the identity and concentration of other components present in the composition and the like. The concentration of surfactant component may be in the range of about 0.01% w/v or less to about 1 or about 5% w/v or more. Care should be taken to avoid using excessive amounts of surfactant component since this is wasteful and/or can have a detrimental effect on the contact lens being cared for or on the wearer of the contact lens. The surfactant component is preferably soluble in the present compositions, which are preferably solutions.

The enzyme or enzymes used are capable of removing at least one type of deposit material from a contact lens. The amount of such enzyme or enzymes used is preferably effective to remove substantially all of at least one type of deposit material from a deposit material laden contact lens in a reasonable time, preferably within about 12 hours, for example, in the range of about 1 minute to about 12 hours, and more preferably within about 2 hours, for example, about 1 minute to about 2 hours. The active enzyme-containing liquid medium preferably contains sufficient enzyme to provide between about 0.0001 to about 5 Anson units of activity, more preferably between about 0.001 or about 0.01 to about 0.1 or about 1 Anson unit, per single lens treatment. Higher or lower amounts may be used.

The enzyme employed may be selected from enzymes which are conventionally employed in the enzymatic cleaning of contact lenses. For example, many of the enzymes disclosed in Huth et al Reissue U.S. Pat. No. 32,672 and Karageozian et al U.S. Pat. No. 3,910,296 are useful in the present invention. Each of these patents is incorporated in its entirety herein by reference. Among the useful enzymes are those selected from proteolytic enzymes, lipases and mixtures thereof. The enzyme may be one or more carbohydrate-active or carbolytic enzymes. Specific examples of useful enzymes include proteases, amylases, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Keay, L., Moser, P. W. and Wildi, B. S., "Proteases of the Genus Bacillus. II Alkaline Proteases", Biotechnology and Bioengineering, Vol. XII, pp. 213–249 (1970) and Keay, L. and Moser, P. W., "Differentiation of Alkaline Proteases from Bacillus Species" Biochemical and Biophysical Research Comm., Vol. 34, No. 5, pp. 600–604 (1969).

The Subtilisin enzymes are broken down into two subclasses, subtilisin A and subtilisin B. In the subtilisin A grouping are enzymes derived from such species are *B. subtilis*, *B. licheniformis* and *B. pumilis*. Organisms in this subclass produce little or no neutral protease or amylase. The subtilisin B. sub-class is made up of enzymes from such organisms a *B. subtilis*, *B. subtilis* var. *amylosacchariticus*, *B. amyloliquefaciens* and *B. subtilis* NRRL B3411. these organisms produce neutral proteases and amylases on a level about comparable to their alkaline protease production. One or more enzymes from the subtilisin A sub-class are particularly useful.

In addition, other preferred enzymes are, for example, pancreatin, trypsin, collagenase, keratenase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of deposit material from a lens deposited due to normal wear. This standard is stated with reference to contact lens wearers with a history of normal pattern of lens deposit material accretion, not the very small group who may at one time or another have a significantly increased rate of deposit material accretion such that cleaning is recommended every day, or every two or three days.

The amount of enzyme required to make an effective lens cleaner will depend on several factors, including the inherent activity of the enzyme.

Enzyme activity is pH dependent so for any given enzyme, there is a particular pH range in which that enzyme will function best. The determination of such range can readily be done by known techniques.

The disinfecting contacting preferably occur at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contacting preferably occur at or about atmospheric pressure. The disinfecting contacting preferably occurs for a time to substantially completely disinfect the lens being treated. Such contacting times can be in the range of about 0.1 hours to about 12 hours or more. The cleaning contacting preferably occurs for a time to substantially clean the lens of at least one type of deposit material, e.g., in the range of about 0.2 hours to about 12 hours or more.

The following non-limiting examples illustrate certain aspects of the present invention.

EXAMPLE 1

A solution is prepared by blending the various components together and has the following composition:

Sodium carboxymethyl cellulose (USP) 0.2% (w/v)

Sodium chlorite (technical grade) 0.0625% (w/v)

Sodium chloride (USP) 0.75% (w/v)

Hydrochloric acid or sodium hydroxide pH adjusted to 7.4

Boric acid (NF) 0.15% (w/v)

Purified water (USP) Q.S. to volume

When it is desired to disinfect a contact lens, it is placed in a conventional lens container suitable for storing the lens. A 10 ml quantity of the solution is placed in the lens container. After six (6) hours, the lens is removed from the lens container and placed directly in a human eye. It is found that the treated contact lens is disinfected and is suitable for safe and comfortable wear in the eye.

The chlorite component alone exhibits bactericidal activities as well as fungicidal activities which are non-irritating and non-toxic in the eye. This chlorite component can be used as an effective and safe disinfectant for contact lens. The antimicrobial activity of a solution containing the chlorite component is observed to be substantially directly proportional to the concentration of the chlorite component.

In addition, it has been found that when polyanionic components, such as carboxymethyl cellulose, are formulated with chlorite components the formulation effectively reduces oxidation induced damage to the contact lens as well as reducing and/or delaying protein deposit formation on the contact lens surface. Further, such formulations provide significantly improved cytotoxic response, that is are less cytotoxic, relative to such formulations without the polyanionic components. Also such formulations are stable at 25° C. and 45° C. for long periods of time, on the order of 2 years or more.

Thus, formulations including effective contact lens disinfecting amounts of chlorite components and synthetic or natural water soluble polyanionic components, such as polymers of this type, can be used as effective, non-irritating, non-toxic, safe and efficacious single bottle contact lens disinfection systems which provide long lasting and enhanced soothing and lubrication during contact lens wear.

EXHIBIT 2

Example 1 is repeated except that the solution additionally includes 0.00085% (w/v) of vitamin B-12.

Substantially the same results are obtained using this solution as are obtained using the solution of Example 1. In addition, the solution of this Example 3 has a distinctive rose color.

EXAMPLE 3

Example 1 is repeated except that the solution additionally includes the following metal ions (added as the metal chlorides):

Potassium ion (K$^+$) 18.2 millimolar

Magnesium ion (Mg$^{++}$) 0.3 millimolar

Calcium ion (Ca$^{++}$) 0.7 millimolar

Substantially the same results are obtained using this solution as are obtained using the solution of Example 1.

EXHIBIT 4

Example 3 is repeated except that the solution additionally includes 0.00085% (w/v) of vitamin B-12.

Substantially the same results are obtained using this solution as are obtained using the solution of Example 3. In addition, the solution of this Example 4 has a distinctive rose color.

EXAMPLE 5

A solution is prepared by blending the various components together and has the following composition:

Sodium carboxymethyl cellulose (USP) 0.5% (w/v)

Stabilized chlorine dioxide [1] (0.005% (w/v)

[1] Product sold by Bio-Cide International Inc., under the trademark PUROGENE®.

Sodium chloride (USP) 0.62% (w/v)

Boric acid 0.2% (w/v)

Potassium chloride (USP) 0.14% (w/v)

Calcium chloride dihydrate (USP) 0.02% (w/v)

Magnesium chloride hexahydrate (USP) 0.006% (w/v)

Sodium hydroxide (NF) adjust to pH 7.6

Purified water Q.S. to volume

A quantity, for example, 20 ml, of this solution is placed in a conventional flexible or squeezable container used to dispense eye drops. A contact lens wearer periodically places one or more drops of the solution from the container in her eyes wearing contact lenses, as needed to provide the desired degree of wetness.

This solution is found to be an effectively preserved rewetting eye drop formulation. In addition, although the solution is effectively preserved, it is ophthalmically acceptable and is, in fact, soothing to the eye. The polyanionic component, sodium carboxymethyl cellulose, is effective in this solution in mitigating against free radical and/or oxidative damage to the eye. Thus, the polyanionic components in combination with the chlorite components provide for relatively long lasting protection of the eye and/or contact lens without detrimentally affecting the preservative effectiveness of the chlorite components.

It has been found that chlorite components can be used as effective, non cytotoxic and non-irritating preservatives for polyanionic component-containing rewetting eye drop formulations, particularly in multi-dose product configurations.

EXAMPLE 6

Example 5 is repeated except that the solution additionally includes 0.00085% w/v of vitamin B-12.

Substantially the same results are obtained using this solution as are obtained using the solution of Example 5. In addition, the solution of this Example 6 has a distinctive rose color.

EXAMPLE 7

A solution is prepared by blending the various components together and has the following composition:

Sodium chlorite (technical grade) 0.0225% (w/v)

Sodium carboxymethyl cellulose (USP) 0.2% (w/v)

Sodium chloride (USP) 0.75% (w/v)

Boric acid (NF) 0.15% (w/v)

Hydrochloric acid or Sodium hydroxide Adjust to pH 7.4

Purified water (USP) Q.S. to volume

A quantity of this solution is placed, together with a daily disposable contact lens, in a conventional daily disposable contact lens package useful for transporting, storing (prior to use) and dispensing daily disposable contact lenses. The lens remains in the package until it is removed from the package and placed directly into the eye for safe and comfortable wear. The solution may be used in transporting and/or storing and/or dispensing all other contact lens types and wear modalities.

The solution is found to be an effectively preserved contact lens storage medium. The lenses are maintained sterile in the solution, and the solution facilitates, for example, provides enhanced lubricity to make more comfortable, the wearing of the lens in the eye. More specifically, the solution remains stable and is effectively preserved with the sodium carboxymethyl cellulose substantially intact for more than 6 months at 45° C. Sodium chlorite is a mild oxidant of non-radical nature and exhibits antimicrobial activities against bacteria and fungi adequate for a safe and efficacious preservative for the lens storage solution. Furthermore, it has also been found that the polyanionic component, for example, sodium carboxymethyl cellulose, effectively quenches oxygen radicals which reduces any radical induced oxidative damage in the eye and, thus, provides added comfort for contact lens wearers in addition to providing beneficial lubricity effects in the eye.

The in-the-eye protective effects of the polyanionic component, sodium carboxymethyl cellulose, are relatively long lasting due to its strong binding affinity toward the polymer making up the contact lens. Thus, when formulated to include both the chlorite and the polyanionic component, as in the solution of this Example 4, the cytotoxicity response and the human clinical response is improved significantly over the use of a similar composition without the polyanionic component. Additionally, results of animal (rabbit) ocular safety studies with such a combination solution indicate no adverse effects with an exaggerated multiple topical instillation to the eye with a soft contact lens four (4) times a day following 28 consecutive days of testing.

The solution is an effective, non-toxic, non-irritating and comforting (soothing and lubricating) storage medium for dispensing new soft and rigid gas permeable contact lenses, for example, daily disposable contact lenses.

EXAMPLE 8

Example 7 is repeated except that the solution additionally includes 0.00085% (w/v) of vitamin B-12.

Substantially the same results are obtained using this solution as are obtained using the solution of Example 7. In addition, the solution of this Example 8 has a distinctive rose color.

EXAMPLE 9

Example 7 is repeated except that the solution additionally includes the following metal ions (added as the metal chlorides):

Potassium ion ($K^+$) 18.2 millimolar
Magnesium ion ($Mg^{++}$) 0.3 millimolar
Calcium ion ($Ca^{++}$) 0.7 millimolar Substantially the same results are obtained using this solution as are obtained using the solution of Example 1.

EXAMPLE 10

Example 9 is repeated except that the solution additionally includes 0.00085% (w/v) of vitamin B-12.

Substantially the same results are obtained using this solution as are obtained using the solution of Example 9. In addition, the solution of this Example 10 has a distinctive rose color.

While this invention has been described with respect to various specific examples and embodiments, it is to be understood that the invention is not limited thereto and that it can be variously practiced with the scope of the following claims.

What is claimed is:

1. A composition comprising:
    a liquid medium;
    a chlorite component in said liquid medium in an effective contact lens disinfecting amount; and
    a polyanionic component in said liquid medium in an amount of at least about 0.0% w/v effective to do at least one of:
        reduce the toxicity of said composition to the human eye; and reduce the damage to a contact lens caused by immersing the contact lens in said composition, provided that said polyanionic component and any precursor thereof do not act to substantially delay the release of another component in the composition or any liquid-containing precursor thereof, said polyanionic component comprises a polymeric material having multiple anionic charges, and said composition having a viscosity of less than 50 cps at 25° C. and an osmolality of at least about 200 mOsmol/kg.

2. The composition of claim 1 which further comprises a vitamin B-12 in an amount effective to provide a distinctive color to said composition.

3. The composition of claim 1 wherein said liquid medium comprises water, said chlorite component and said polyanionic component are water soluble, said chlorite component is present in an amount of about 0.15% w/v or less, and said composition includes an effective amount of a tonicity adjusting component and an effective amount of a pH buffering component, and has a pH in the range of about 6 to about 9.

4. The composition of claim 1 wherein said polyanionic component is selected from the group consisting of anionic cellulose derivatives, anionic polymers derived from acrylic acid, anionic polymers derived from methacrylic acid, anionic polymers derived from alginic acid, anionic polymers derived from amino acids and mixtures thereof.

5. The composition of claim 1 wherein said polyanionic component comprises a carboxymethyl cellulose.

6. The composition of claim 1 which further comprises an effective amount of a mineral component selected from the group consisting of potassium components, magnesium components, calcium components and mixtures thereof to enhance the wearability of a contact lens disinfected using said composition.

7. A composition comprising:
    a liquid medium;
    a chlorite component in said liquid medium in an effective preserving amount; and
    a polyanionic component in said liquid medium in an amount of at least about 0.01% w/v effective to enhance the lubricity of said composition and to reduce the cytotoxicity of said composition to the human eye, provided that said polyanionic component and any precursor thereof do not act to substantially delay the release of another component in the composition or any liquid-containing precursor thereof, said polyanionic component comprises a polymeric material having multiple anionic charges, said composition having a viscosity of less than 50 cps at 25° C. and an osmolality of at least 200 mOsmol/kg and including substantially no free chlorine dioxide.

8. The composition of claim 7 wherein said liquid medium comprises water and which composition includes an effective amount of a tonicity adjusting component and an effective amount of a pH buffering component, and has a pH in the range of about 6 to about 9 and said chlorite component is present in an amount of 0.15% or less.

9. The composition of claim 7 wherein said composition is ophthalmically acceptable and is adapted for in-the-eye use, and further includes an effective amount of a mineral component selected from the group consisting of potassium components, magnesium components, calcium components and mixtures thereof to enhance the wearability of a contact lens contacted with said composition.

10. The composition of claim 9 wherein said composition is in the form of a multi-dose rewetting eye drop formulation.

11. The composition of claim 7 wherein said composition is in the form of a contact lens storage formulation.

12. The composition of claim 7 which further comprises a vitamin B-12 in an amount effective to provide a distinctive color to said composition.

13. The composition of claim 7 wherein said polyanionic component is selected from the group consisting of anionic cellulose derivatives, anionic polymers derived from acrylic acid, anionic polymers derived from methacrylic acid, anionic polymers derived from alginic acid, anionic polymers derived from amino acids and mixtures thereof.

14. The composition of claim 7 wherein said polyanionic component comprises a carboxy methylcelluloses.

15. A method for treating an eye wearing a contact lens comprising administering to said eye an effective amount of the composition of claim 1.

16. The method of claim 15 wherein said polyanionic component is selected from the group consisting of carboxymethyl celluloses and mixtures thereof.

17. A composition comprising:
    a liquid medium;
    a chlorite component in said liquid medium in an effective contact lens disinfecting amount;

a polyanionic component in said liquid medium in an amount of at least about 0.01% w/v effective to do at least one of:

reduce the toxicity of said composition to the human eye, and reduce the damage to a contact lens caused by immersing the contact lens in said composition;

an effective amount of a tonicity adjusting component, said composition having an osmolality of at least about 200 mOsmol/kg; and an effective amount of a mineral component selected from the group consisting of potassium components, magnesium components, calcium components and mixtures thereof to enhance the wearability of a contact lens disinfected using said composition, said mineral component being present in an amount in a range of about 50% to about 200% of the concentration of the mineral component, based on metal ion, in average human tear fluid.

18. The composition of claim 17 wherein said chlorite component is present in an amount of about 0.15% w/v or less, and said composition further comprises vitamin B-12 in an amount effective to provide a distinctive color to said composition.

19. The composition of claim 17 wherein said liquid medium comprises water, said chlorite component and said polyanionic component are water soluble, said polyanionic component is selected from the group consisting of polymeric materials having multiple anionic charges and mixtures thereof, and said composition includes an effective amount of a pH buffering component and has a pH in the range of about 6 to about 9.

20. The composition of claim 17 wherein said polyanionic component comprises a carboxymethyl cellulose.

21. A composition comprising:

a liquid medium;

a chlorite component in said liquid medium in an effective preserving amount;

a polyanionic component in said liquid medium in an amount of at least about 0.01% w/v effective to enhance the lubricity of said composition and to reduce the cytotoxicity of said composition to the human eye;

an effective amount of a tonicity adjusting component, said composition having an osmolality of at least about 200 mOsmol/kg; and an effective amount of a mineral component selected from the group consisting of potassium components, magnesium components, calcium components and mixtures thereof to enhance the wearability of a contact lens contacted with said composition, said mineral component being present in an amount in a range of about 50% to about 200% of the concentration of the mineral component, based on metal ion, in average human tear fluid, said composition including substantially no free chlorine dioxide.

22. The composition of claim 21 wherein said chlorite component is present in an amount of about 0.15% or less and said composition includes an effective amount of a pH buffering component and has a pH in the range of about 6 to about 9.

23. The composition of claim 21 wherein said composition is in the form of a multi-dose rewetting eye drop formulation.

24. The composition of claim 21 wherein said liquid medium comprises water, and said chlorite component and said polyanionic component are water soluble, and said polyanionic component comprises a polymeric material.

25. The composition of claim 21 wherein said polyanionic component comprises a carboxymethyl cellulose.

26. The composition of claim 1 wherein said polyanionic component is effective to reduce the toxicity of said composition to the human eye; and reduce the damage to a contact lens caused by immersing the contact lens in said composition.

27. The composition of claim 17 wherein said polyanionic component is effective to reduce the toxicity of said composition to the human eye; and reduce the damage to a contact lens caused by immersing the contact lens in said composition.

28. The composition of claim 1 which includes substantially no free chlorine dioxide.

29. The composition of claim 17 which includes substantially no free chlorine dioxide.

30. A method for storing a contact lens comprising immersing the contact lens in an effective amount of the composition of claim 1.

31. The method of claim 30 wherein said polyanionic component is selected from the group consisting of carboxymethyl celluloses and mixtures thereof.

32. A method for disinfecting a contact lens comprising contacting the contact lens with an effective amount of the composition of claim 1.

* * * * *